United States Patent
Hart et al.

(10) Patent No.: US 6,743,210 B2
(45) Date of Patent: *Jun. 1, 2004

(54) STENT DELIVERY CATHETER POSITIONING DEVICE

(75) Inventors: Colin P. Hart, Queensbury, NY (US); Kevin C. Martin, Stillwater, NY (US); Ryan M. LeClair, Delmar, NY (US); Mark H. Van Diver, Argyle, NY (US); Glenn H. Wadleigh, Queensbury, NY (US); Bill A. Wetherbee, Queensbury, NY (US)

(73) Assignee: SciMed Life Systems, Inc., Maple Grove, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 153 days.

(21) Appl. No.: 09/784,762

(22) Filed: Feb. 15, 2001

(65) Prior Publication Data
US 2002/0111666 A1 Aug. 15, 2002

(51) Int. Cl.$^7$ .............................................. A61M 25/10
(52) U.S. Cl. ...................... 604/194; 623/1.11
(58) Field of Search ................... 606/1, 194, 192; 623/1.11; 604/96.01

(56) References Cited

U.S. PATENT DOCUMENTS

| | | | |
|---|---|---|---|
| 4,547,194 A | 10/1985 | Moorehead | 604/283 |
| 4,572,186 A | 2/1986 | Gould et al. | 128/341 |
| 4,962,757 A * | 10/1990 | Stefan | 604/174 |
| 5,129,887 A | 7/1992 | Euteneuer et al. | 606/194 |
| 5,290,248 A | 3/1994 | Bierman et al. | 604/174 |
| 5,391,172 A | 2/1995 | Williams et al. | 606/108 |
| 5,507,768 A | 4/1996 | Lau et al. | 606/198 |
| 5,558,101 A | 9/1996 | Brooks et al. | 728/772 |
| 5,579,780 A | 12/1996 | Zadini et al. | 128/772 |
| 5,690,645 A | 11/1997 | Van Erp | 606/108 |
| 5,735,819 A * | 4/1998 | Elliott | 604/161 |
| 5,776,142 A | 7/1998 | Gunderson | 606/108 |
| 5,921,968 A | 7/1999 | Lampropoulos et al. | 604/246 |
| 5,980,532 A | 11/1999 | Wang | 606/108 |
| 5,980,533 A | 11/1999 | Holman | 606/108 |
| 6,007,543 A | 12/1999 | Ellis et al. | 606/108 |
| 6,612,624 B1 * | 9/2003 | Segal et al. | 285/330 |

FOREIGN PATENT DOCUMENTS

| | | |
|---|---|---|
| EP | 0 627 201 B1 | 12/1994 |
| EP | 0 873 733 A1 | 10/1998 |
| WO | WO 98/11846 | 3/1998 |
| WO | WO 00/67675 | 11/2000 |

\* cited by examiner

*Primary Examiner*—Michael H. Thaler
(74) *Attorney, Agent, or Firm*—Crompton, Seager & Tufte, LLC

(57) ABSTRACT

The present invention generally relates to a medical device and procedure for accurately positioning a catheter across a desired region within a patient's vasculature. In particular, the present invention provides a hub assembly unit that allows a physician to precisely position a stent within a vessel utilizing a stent delivery catheter. The hub assembly unit includes a fine adjustment mechanism. The fine adjustment mechanism extends or contracts the length of the hub assembly unit in controlled incremental units. These controlled fine displacements are then translated directly to the stent delivery or balloon dilation catheter.

21 Claims, 3 Drawing Sheets

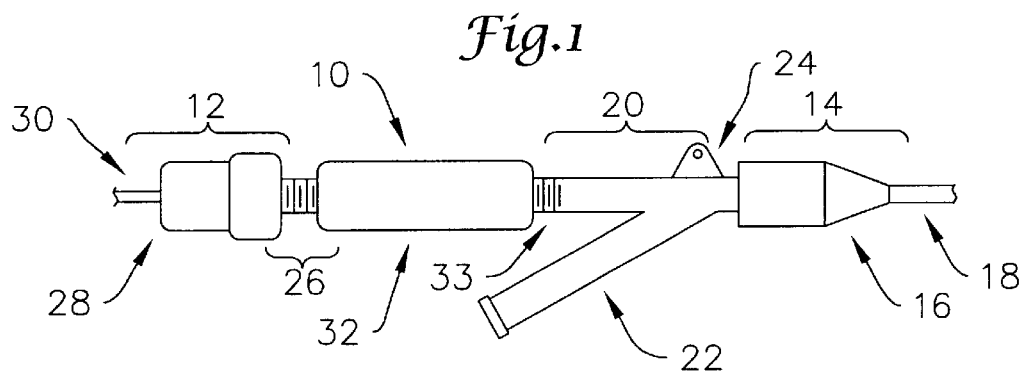
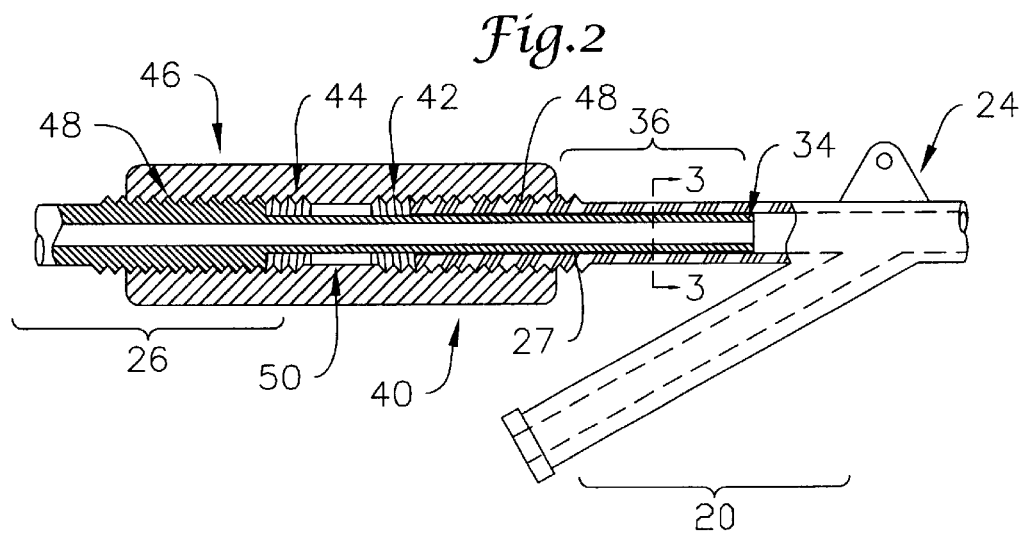
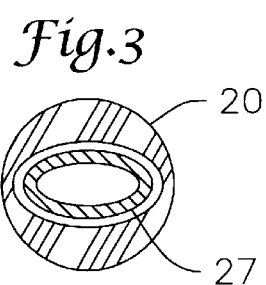
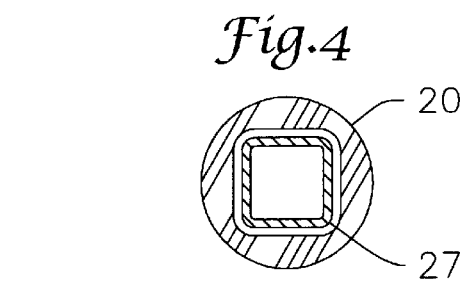
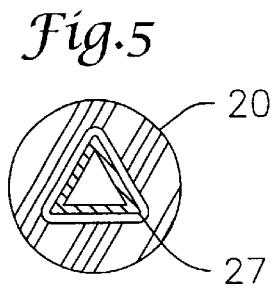

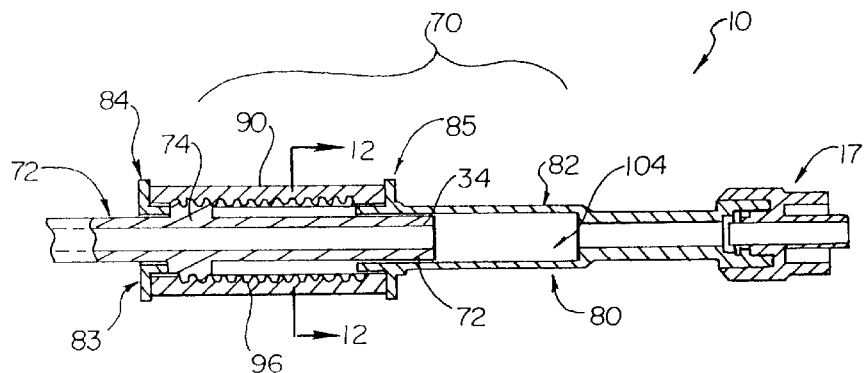
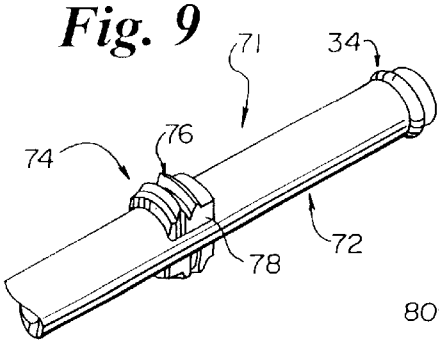
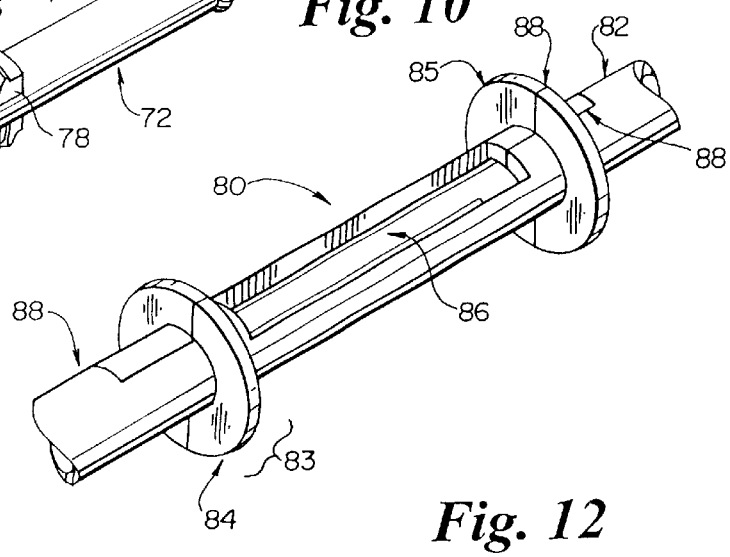
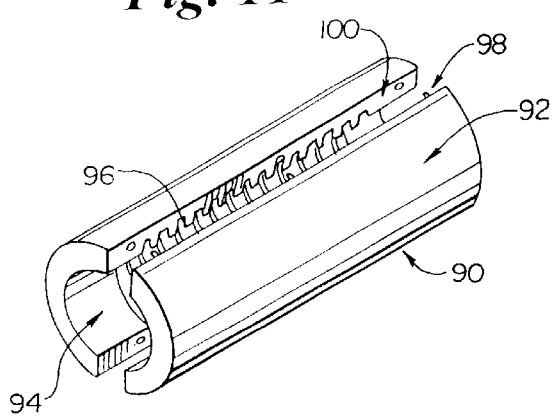
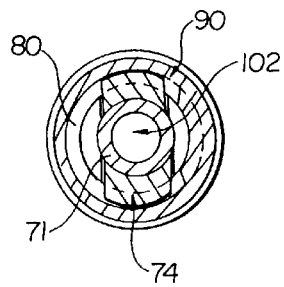

STENT DELIVERY CATHETER POSITIONING DEVICE

FIELD OF INVENTION

The present invention generally relates to a medical device for positioning a stent delivery or dilatation balloon catheter within the vascular system of a patient. More specifically, the present invention discloses a hub assembly unit providing an operator the ability to finely adjust the positioning of a stent delivery or a balloon dilation catheter within a patient's vascular system.

BACKGROUND OF THE INVENTION

Percutaneous Transluminal Coronary Angioplasty (PTCA) is a well-established procedure for dilating stenosed vessel regions within a patient's vasculature. In this procedure, a balloon angioplasty catheter is introduced into the vasculature, typically through an incision in the femoral artery in the groin. The balloon catheter is then advanced through the femoral artery, through the aortic arch, and into the artery to be treated. The balloon portion of the dilation catheter is specifically advanced across the stenosis or constricted vessel, wherein the balloon is inflated. Inflation of the balloon dilates the surrounding vessel and/or displaces the plaque the forms the stenosis. The resulting treated vessel is then characterized by a greater cross-sectional area permitting additional blood flow through the previously occluded or constricted region.

Over a period, a previously dilated vessel may narrow. Often this narrowing is a result of a vessel "rebounding" from an angioplasty procedure. In order to prevent vessel rebounding, stents are often deployed concurrently with a vessel dilation procedure. A stent is positioned across the treated dilated region of vasculature where it is radially expanded utilizing a stent delivery catheter. Once properly seated within the vessel wall, the frame of the stent opposes any inward radial forces associated with vessel rebounding.

During a PTCA procedure, it is often necessary to finely adjust the positioning of the stent delivery or balloon dilatation catheter. Improper placement of a stent within a desired region can cause a portion of the treated vessel to narrow, substantially decreasing the benefits of the initial medical procedure.

Currently, a physician positions the distal end of a balloon dilatation or stent delivery catheter by manually pushing or pulling on the proximal end of the catheter. These pushing and pulling motions must be transmitted through the entire length of the catheter shaft to affect the catheter's distal tip. The catheter shaft in a medical procedure, however, is usually quite intricately routed within a patient's vascular system. The vascular pathlength from the femoral artery to the desired treatable artery is usually long and quite tortuous. Manipulations made by the physician at the catheter's proximal end, therefore, do not necessarily directly translate to the same movements at the catheter's distal end.

Catheters have a natural tendency to compress or elongate irregularly when manipulated proximally. More specifically, when advancing a catheter from the catheter's proximal end, the catheter tends to advance into and through the curves of vessel walls where they contact a greater surface area. An advancing catheter, therefore, requires greater force and displacement at the catheter's proximal end to move the catheter a desired length at the catheter's distal end. In contrast, a retracting catheter straightens through the curvature of vessel walls causing the catheter to elongate when withdrawn.

A physician is often required to make a series of advancements and retractions of the catheter to effectively navigate through the tortuous vascular system of a patient. Each advancement and retraction compresses or elongates various sections of the catheter. These compressions and elongations store potential energy throughout the length of the catheter shaft. Coarse manipulations by a physician at the catheter's proximal end may affect the arrangement of these compressions and elongations. Specifically, pulling and pushing of the proximal end of a catheter may cause an unaccounted for release of stored potential energy in the catheter shaft. This unaccounted for release of energy is called the "backlash" phenomenon. Backlash causes a physician to experience either a sudden burst or a lag in relative movement of the distal end of the catheter. This unaccounted for release functionally decreases accuracy in positioning a catheter within a patient's vascular system. Further, even without the issues related to stored energy and backlash, making the necessary fine adjustments requires more time and is less accurate than desirable.

Further complications arise when a physician attempts to inflate the stent delivery or balloon dilation catheter. Before inflation, a physician must tighten the hemostasis valve around the catheter. Tightening the hemostasis valve, however, may cause the stent delivery catheter to move out of position. Consequently, the physician is forced to reposition the catheter once again across the desired vascular region. As a result, the time spent repositioning the distal end of a catheter causes unnecessary medical expense and further trauma to the patient.

SUMMARY OF THE INVENTION

The present invention provides a medical device permitting fine adjustments of the distal end of a stent deployment or balloon dilatation catheter. In particular, the present invention discloses a hub assembly unit providing a fine adjustment mechanism. The fine adjustment mechanism extends or contracts the length of the hub assembly unit in controlled incremental units. These controlled fine displacements are then translated directly to the stent delivery or balloon dilation catheter.

Contrary to coarse adjustments, fine displacements have been found to conserve stored potential energy within a catheter system. A physician may therefore incrementally adjust the displacement of the hub assembly unit of the present invention to accurately and predictably advance or withdraw a stent delivery or balloon dilation catheter. In the present invention, fine adjustments made at the proximal end of the hub assembly unit directly translate to similar adjustments at the distal end of the catheter. Thus, the hub assembly unit of the present invention allows a physician to precisely position a stent delivery or balloon dilation catheter at a desired point within a desired region of a patient's vasculature.

BRIEF DESCRIPTION OF THE DRAWINGS

FIG. 1 shows a side elevation view of a hub assembly unit of the present invention, the hub assembly unit being attached to the proximal end of a guide catheter and further receiving a stent delivery catheter at the hub assembly unit's proximal end;

FIG. 2 shows an enlarged cross-sectional elevation view of a turnbuckle style fine adjustment mechanism embodiment of the hub assembly unit;

FIG. 3 shows a transverse cross-sectional view of a tubular section of the hub assembly unit of the present invention, the tubular section having a lumen of oval shape;

FIG. 4 shows a transverse cross-sectional view of a tubular section of the hub assembly unit of the present invention, the tubular section having a lumen of rectangular shape;

FIG. 5 shows a transverse cross-sectional view of a tubular section of the hub assembly unit of the present invention, the tubular section having a lumen of triangular shape;

FIG. 8 shows a cross-sectional elevation view of a slot and key style fine adjustment mechanism embodiment of the hub assembly unit of the present invention;

FIG. 9 shows a partial key element of the slot and key style fine adjustment mechanism of the present invention comprising a partially threaded key;

FIG. 10 shows a slotted track element of the slot and key style fine adjustment mechanism comprising a slotted track in which the partial key element travels within;

FIG. 11 shows a threading nut element for the slot and key style fine adjustment mechanism, the threading nut element comprising two reversibly attaching cylindrical halves that mate when assembled with the partially threaded key of the partial key element; and FIG. 12 shows a transverse cross-sectional view of the slot and key style fine adjustment mechanism illustrating the seating relationships between the partial key element, the slotted track element and the threading nut element.

DETAILED DESCRIPTION OF THE INVENTION

Figure 6:
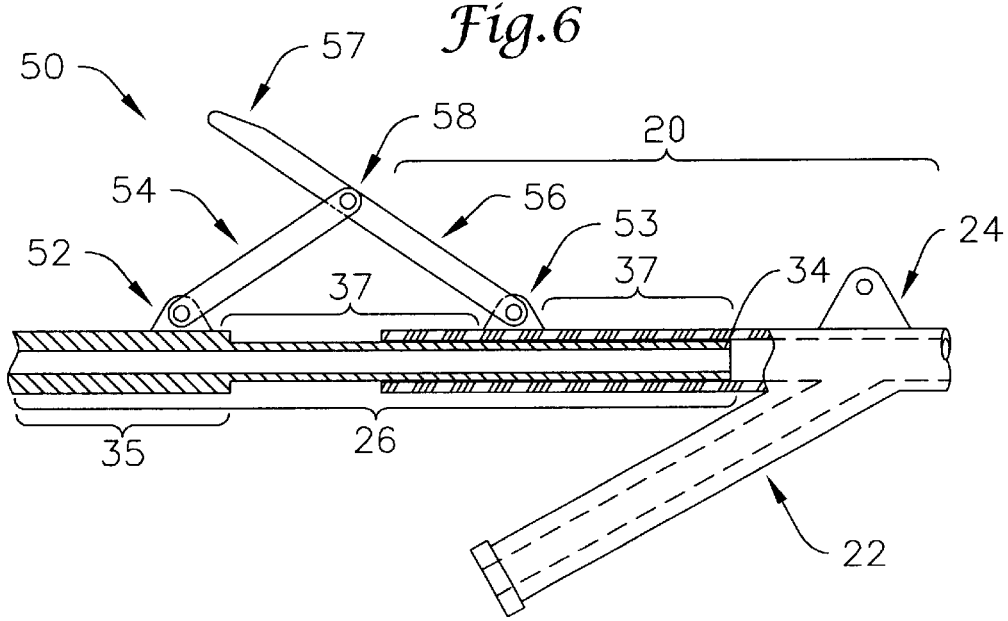
FIG. 6 shows a cross-sectional elevation view of an additional embodiment of the hub assembly unit of the present invention comprising a lever style fine adjustment mechanism.

The following detailed description should be read with reference to the drawings, in which like elements in different drawings are numbered identically. The drawings, which are not necessarily to scale, depict selected embodiments and are not intended to limit the scope of the invention. Examples of constructions, materials, dimensions and manufacturing processes are provided for selected elements. Those skilled in the art will recognize that many of the examples provided have suitable alternatives that may be utilized.

Referring now to the drawings, FIG. 1 shows one embodiment of a hub assembly unit 10 of the present invention. Hub assembly unit 10 comprises a proximal end 12 and a distal end 14. Distal end 14 includes a linking mechanism 16 connecting hub assembly unit 10 to a first medical device 18. In preferred embodiments, first medical device 18 is a catheter, and more specifically, a guide catheter. A proximal fitting is positioned at the proximal end of guide catheter 18 for attaching and fluidly connecting ancillary apparatus to the lumen of guide catheter 18. The proximal fitting generally includes at least one male or female threaded region on the proximal fitting. Referring specifically to FIG. 1, the proximal fitting of guide catheter 18 comprises a female luer type fitting (not shown). As a result, distal end 14 of hub assembly unit 10 comprises a male luer type fitting (not shown) to properly mate and seat within the guide catheter's proximal fitting. In certain embodiments, the union between hub assembly unit 10 and guide catheter 18 is completed using alternative connectors. Additional attaching mechanisms between hub assembly unit 10 and guide catheter 18, being known in the art, are also incorporated as within the scope of the present invention. In an alternative embodiment, hub assembly unit 10 is permanently affixed to the body of guide catheter 18.

Proximally from the proximal end of the guide catheter 18 is a first tubular section 20 of hub assembly unit 10. First tubular section 20 comprises a proximal end, a distal end and further comprising a lumen extending the length therethrough. The distal end of first tubular section 20 includes either a male or a female connector that mates with the proximal fitting of guide catheter 18. In certain additional embodiments, first tubular section 20 further comprises a Y-adapter 22. Y-adapter 22 includes a molded section that permits additional medical apparatus access to the internal lumen of hub assembly unit 10, and furthermore, access to the lumen of guide catheter 18 when so attached.

First tubular section 20 may additionally comprise a means for securing hub assembly unit 10 during a medical procedure. Proper operation of hub assembly unit 10 requires maintaining hub assembly unit 10 in a single or fixed position, relative to the patient, during adjustment of the hub assembly during a medical procedure. Medical personnel often hold and maintain the position of hub assembly unit 10 in this proper relationship during the medical procedure. A suture ring 24, however, may mechanically maintain the positioning of hub assembly unit 10, thereby freeing up medical personnel during the medical procedure. Other mechanical means such as tape and clamps may likewise be used to secure hub assembly unit 10 during the medical procedure.

Proximal end 12 of hub assembly unit 10 comprises a second tubular section 26 having a proximal end, a distal end and a lumen extending the length therethrough. The proximal end of second tubular section 26 preferably includes a hemostasis valve 28, or other fitting capable of maintaining the position and orientation of second medical device 30 inserted therein. As shown in FIG. 2, second tubular section 26 preferably includes a tubular extension or section 27 slidably disposed within the lumen of the first tubular section 20. Second medical device 30 is advanced to a desired region within a patient's vasculature by initially inserting second medical device 30 into the proximal end of second tubular section 26. Second medical device 30 is advanced through the lumen of second tubular section 26, through the lumen of first tubular section 20, and finally through the lumen of guide catheter 18, until finally reaching a desired region within the patient's vasculature. In one embodiments of the present invention, second medical device 30 is a stent delivery catheter. In an alternative embodiment of the present invention, second medical device 30 is a balloon dilation catheter.

Hemostasis valve 28, or the like, mechanically constricts about the outer diameter of second medical device 30, hermetically sealing the atmospherically exposed portion of second medical device 30 from the internally advanced portions of second medical device 30. This hemostatic measure concurrently affixes second medical device 30 into a single longitudinal and rotational orientation. The mechanical pressure applied by hemostatsis valve 28 maintains this single orientation while hemostasis valve 28 is actively engaged with second medical device 30.

Fine adjustment mechanism 32 connects and maintains the position of the proximal end of first tubular section 20 with or relative to the distal end of second tubular section 26.

Fine adjustment mechanism 32 additionally engages either first tubular section 20, second tubular section 26, or both tubular sections. Fine adjustment mechanism 32 additionally provides a mechanical means for displacing the two tubular sections with respect to one another. In particular, fine adjustment mechanism 32 extends or contracts the length of hub assembly unit 10 by displacing the spatial relationship between first tubular section 20 and second tubular section 26. As shown, internal threads on the fine adjustment mechanism mate with threads on the two tubular sections and functions as a turnbuckle when rotated to draw the member together or apart.

In preferred embodiments, fine adjustment mechanism 32 may expand or contract the length of hub assembly unit 10 by a total of 1 to 3 centimeters. Most preferably, hub assembly unit 10 may be displaced a total of 1 to 2 centimeters. Units of measurement 33 are placed upon hub assembly unit 10 to aid physicians in gauging spatial displacement of hub assembly unit 10 during a medical procedure.

In a preferred embodiment, a guide catheter is first advanced to a desired region within a patient's vasculature. Hub assembly unit 10 is then attached to the proximal end of the advanced guide catheter, if not already attached. A second medical device 30 is then advanced to a desired region within the patient's vasculature by initially inserting the second medical device 30 into the proximal end of second tubular section 26 of hub assembly unit 10. The second medical device 30 is then advanced through the lumen of second tubular section 26, through the lumen of first tubular section 20, and finally through the lumen of guide catheter 18. Second medical device 30 is then coarsely positioned at approximately the desired region within a patient's vasculature.

A physician may make coarse adjustments to second medical device 30 by manually pushing and pulling on the proximal end of second medical device 30. Coarse manual adjustments allow a physician to position the distal end of second medical device 30 approximately at a desired point within a desired region within the patient's vasculature. As described earlier, however, the length of second medical device makes precise placement difficult. Manipulations made by the physician at the proximal end of second medical device 30 do not necessarily translate to the same motions at the distal end of second medical device 30. Compression or elongation of second medical device 30, caused by second medical device 30 following the tortuous vasculature of the patient, results in second medical device 30 retaining an unaccountable amount of stored potential energy. Small coarse adjustments, therefore, may release this stored energy causing a physician to overshoot a desired target. The present invention overcomes the problem associated with the release of stored potential energy within an advanced catheter.

After second medical device 30 is coarsely positioned within the patient's vasculature, hemostasis valve 28 is mechanically engaged. Hemostatsis valve 28 hemostatically preferably affixes second medical device 30 into a single longitudinal and rotational orientation. As a result, movements made by hub assembly unit 10 and/or guide catheter 18 are directly translated to the second medical device 30. Fine adjustment mechanism 32 provides for minor spatial advancements or retreats of the catheter system. In particular, fine adjustment mechanism 32 extends or contracts the length of hub assembly unit 10 by displacing the spatial relationship between first tubular section 20 and second tubular section 26. These fine displacements are then translated to second medical device 30.

Contrary to coarse adjustments, fine displacements have been found to conserve stored potential energy within a catheter system. The present invention allows a physician to incrementally adjust the positioning of second medical device 30 within a patient's vasculature. Specifically, a physician may accurately advance or withdraw second medical device 30 by fractions of a millimeter through proper operation of fine adjustment mechanism 32. A physician may incrementally adjust the spatial relationships within hub assembly unit 10 to accurately and predictably advance or withdraw a second medical device up to a total distance of approximately 3 centimeters. Fine adjustments made at the proximal end of a catheter system, therefore, directly translate to similar adjustments at the distal end of the catheter system in the present invention. Thus, hub assembly unit 10 allows a physician to precisely position a second medical device 30 at a desired point within the desired region of a patient's vasculature.

Referring now to FIG. 2, wherein an enlarged cross-sectional elevation view of the turnbuckle style fine adjustment mechanism 40 embodiment is shown. With respect to FIG. 2, a distal portion of second tubular section 26 includes a tubular extension or section 27 that is slidably disposed within the lumen of first tubular section 20. At the distal-most end 36 of second tubular section 26 is an O-ring 34. O-ring 34 engages both second tubular section 26 and the lumen wall of first tubular section 20. When second tubular section 26 is slidably displaced along the length of the lumen of first tubular section 20, O-ring 34 hemostatically prevents or reduces blood or other bodily fluids from being displaced between the outer wall of second tubular section 26 and the inner wall of first tubular section 20. This relationship between first tubular section 20 and second tubular section 26 may likewise be reversed wherein first tubular section 20 may be slidably disposed within the lumen of second tubular section 26. In yet another embodiment, both the proximal-most end of first tubular section 20 and the distal-most end of second tubular section 26 terminate within fine adjustment mechanism 32. In this embodiment, fine adjustment mechanism 32 maintains fluid communication between the two tubular sections, as well as provides a location for the two sections to be slidably disposed.

In the illustrated turnbuckle style fine adjustment mechanism 40, a portion of proximal end 42 of first tubular section 20 and a portion of distal portion 44 of second tubular section 26 are threaded. The direction of threading on tubular section 20 is the reverse of the direction of threading on tubular section 26. One tubular section is right hand threaded and the other tubular section is left hand threaded. Thus, in this particular embodiment, the threading of each tubular section is never the same.

Threading nut 46 overlays the threaded portions 42, 44 of first and second tubular sections 20 and 26. Complementary threads 48, to both left and right handed threaded portions 44 and 42, are manufactured into threading nut 46. In a preferred embodiment, complementary threads 48 are molded into threading nut 46. Complimentary threads 48 extend inwardly from the ends of threading nut 46 to a location approximating the center 50 of threading nut 46. At the center 50, complimentary threads 48 terminate, defining the ends of two threaded tracks.

The threaded tracks provide a pathlength for which threaded tubular sections 42 and 44 may travel. Threaded tubular section 42 and 44 travel along the threaded tracks through the appropriate rotation of threaded nut 46. Rotation of threading nut 46 in a clockwise direction causes both first tubular section 20 and second tubular section 26 to both move either inwardly or outwardly, depending upon the direction of the threads. Inward or outward directional movement occurs in unison because threading nut 46 controls the rate of both threaded tubular sections 42 and 44 at the same time. Likewise, rotation of threading nut 46 in the counter-clockwise direction causes the tubular sections to move in unison in the opposite direction as the first.

When threading nut 46 is rotated, complementary threads 48 guide both threaded tubular sections 42 and 44 along their respective threaded tracks. Since threaded tubular sections 42 and 44 are merely portions of first tubular section 20 and second tubular section 26, respectively, movement of threaded tubular sections 42 and 44 are translated as an extension or contraction of hub assembly unit 10 as a whole. The length of hub assembly unit 10, therefore, may be extended or contracted by the proper rotation of threading nut 46, thereby allowing a physician to precisely position a second medical device 30 at a desired point within a desired region of a patient's vasculature.

Extension of the hub assembly unit 10 is proportional to the length of the threading nut 46. As such, hub assembly unit 10 may be lengthened a distance until the threaded portions 44 and 42 disengage from the threading nut 46. Similarly, the length of hub assembly unit 10 may be contracted until the complementary threading 48 ceases within the center 50 of threading nut 46. In preferred embodiments, turnbuckle style fine adjustment mechanism 40 may expand or contract the length of hub assembly unit 10 by a total of 0.5 to 3 centimeters. Most preferably, hub assembly unit 10 may be displaced a total of 1 to 2 centimeters. Each rotation of threaded nut 46 correlates to an incremental displacement of hub assembly unit 10. In preferred embodiments, each rotation of threaded nut 46 spatially displaces hub assembly unit 10 by 1 to 6 millimeters.

Turnbuckle style fine adjustment mechanism 40 may be modified in order to adjust the rate and distance threaded tubular sections 42 and 44 travel within threaded nut 46. One modification includes manufacturing threads of threaded tubular section 42, and its complementary threads 48 in threaded nut 46, more fine (having more threads per linear centimeter) than the other threaded tubular section 44. As a result of this modification, the rotation of threaded nut 46 causes one threaded tubular section 44 to extend or contract farther and faster than its finely threaded counterpart 42. Likewise, only threaded tubular section 44 and its complementary threads 48 may be manufactured with fine threading.

Operation of turnbuckle style fine adjustment mechanism 40 causes exerted rotational energy performed by threading nut 46 to transfer to surrounding apparatus. In this case, transferred rotational energy tends to affect either first tubular section 20 or second tubular section 26. The present invention channels this rotational energy from threading nut 46 into a longitudinal force that causes the spatial displacement of the two tubular section 20 and 26 within hub assembly unit 10.

Rotational energy has a propensity to remain as rotational energy. Thus, by leaving the above-described system alone, exerted rotational energy from threading nut 46 would cause first tubular section 20 and second tubular section 26 to additionally rotate. In order to transform this rotational energy into other forms of work, the rotational energy must be redirected. The present invention transforms exerted rotational energy into a longitudinal motive force.

Securing suture ring 24, or the like, generally restrains first tubular section 20 to a single orientation. Transferred rotational energy from threading nut 46 is therefore refrained from affecting the rotational orientation of first tubular section 20. Second tubular section 26, however, generally remains free to be affected by such transferred rotational energy. Modifications to the shape of tubular sections 20 and 26 can redirect this transferred rotational energy into a functional, longitudinal motive force.

Referring now to FIG. 3, wherein a transverse cross-sectional view at 3—3 of hub assembly unit 10 is shown. The cross-section taken at 3—3 includes portions of both first tubular section 20 and second tubular section 26. Specifically, the cross-section shows a distal extension 27 of second tubular section 26 seated within first tubular section 20. The inner lumen of first tubular section 20 is non-circular in shape. More specifically, the inner lumen of first tubular section 20 is oval. The outer diameter of second tubular section 26 is complementary oval shaped to properly seat within the inner lumen of first tubular section 20. This non-circular lumen design provides torsional resistance. Specifically, the oval shaped lumen configuration prevents second tubular section 26 from spinning within first tubular section 20 when threading nut 46 is rotated. In effect, the oval-shaped design channels transferred rotational energy from threading nut 46 into a longitudinal motive force. This longitudinal motive force displaces second tubular section 26 and first tubular section 20 in a single longitudinal and rotational plane. Transferred energy is then transformed into work that displaces the two tubular sections 20 and 26 along the manufactured oval shaped lumen pathlength.

FIG. 4 is an additional embodiment showing a transverse cross-sectional view at 3—3 of hub assembly unit 10. The cross-section of this particular embodiment similarly includes portions of both first tubular section 20 and second tubular section 26. Specifically, the cross-section includes the distal extension 27 of second tubular section 26 seated within the lumen of first tubular section 20. In FIG. 4, however, the inner lumen of first tubular section 20 is non-circular rectangular shaped. The outer diameter of second tubular section 26 is complementary rectangular shaped to properly seat within the inner lumen of first tubular section 20. This rectangular shaped lumen design additionally provides torsional resistance within hub assembly unit 10. Specifically, the four elongated regions of the rectangular shaped lumen configuration prevent second tubular section 26 from spinning within first tubular section 20 when threading nut 46 is rotated. The rectangular shaped design further channels transferred rotational energy from threading nut 46 into a longitudinal motive force. This longitudinal motive force displaces second tubular section 26 and first tubular section 20 in a single longitudinal and rotational plane. Transferred energy is then transformed into work that displaces the two tubular sections 20 and 26 along the manufactured rectangular shaped lumen pathlength.

FIG. 5 is yet another embodiment showing a transverse cross-sectional view at 3—3 of hub assembly unit 10. The cross-section of this particular embodiment again includes portions of both first tubular section 20 and second tubular section 26. Specifically, the cross-section includes the distal extension 27 of second tubular section 26 seated within first tubular section 20. In FIG. 5, however, the inner lumen of first tubular section 20 is triangular shape. To properly seat within the inner lumen of first tubular section 20, the outer diameter of second tubular section 26 is complementary triangular shaped. This triangular shaped lumen design additionally provides torsional resistance within hub assembly unit 10. Specifically, the three elongated regions of the triangular shaped lumen configuration prevent second tubular section 26 from spinning within first tubular section 20 when threading nut 46 is rotated. The triangular shaped design further channels transferred rotational energy from threading nut 46 into a longitudinal motive force. This longitudinal motive force displaces second tubular section 26 and first tubular section 20 in a single longitudinal and rotational plane. Transferred energy is then transformed into work that displaces the two tubular sections 20 and 26 along the manufactured triangular shaped lumen pathlength.

The inner lumen of second tubular section 26 need not necessarily be oval shaped, rectangular shaped or triangular shaped (as depicted in FIGS. 3, 4 and 5, respectively). Torsional resistance is an outgrowth of the friction fit between the inner lumen diameter of first tubular section 20 and the outer diameter of second tubular section 26. As a result, the inner lumen configuration of second tubular section 26 may be circular without affecting the torsional resistance characteristics of the present invention provided there is sufficient friction between the members.

Referring now to FIG. 6, wherein a cross-sectional elevation view of an additional embodiment of hub assembly unit 10 is shown comprising a lever style fine adjustment mechanism 50. Lever style fine adjustment mechanism 50 similarly comprises a portion of the proximal-most end of first tubular section 20 and a distal portion of second tubular section 26. The distal portion of second tubular section 26 includes two distinct regions, a first distal portion 35 and a second distal portion 37, both having lumens running the length therein. First distal portion 35 attaches at a proximal end to a hemostasis valve (not shown) or other fitting capable of maintaining the position and orientation of a second medical device inserted the length therethrough. Second distal portion 37, on the other hand, is slidably disposed within the lumen of first tubular section 20. Because second distal portion 37 is slidably disposed within first tubular section 20, the lever style fine adjustment mechanism 50 maintains a fluid connection between the proximal end 12 to the distal end 14 of hub assembly unit 10.

At the distal-most end of second distal portion 37 is a seal, such as an O-ring 34. O-ring 34 engages both the distal-most end of second distal portion 37 and the lumen wall of first tubular section 20. When the distal-most end of second distal portion 37 is slidably displaced along the length of the lumen of first tubular section 20, O-ring 34 hemostatically prevents blood or other bodily fluids from being displaced between the outer wall of the distal-most end of second distal portion 37 and the inner wall of first tubular section 20.

With particularity to FIG. 6, lever style fine adjustment mechanism 50 is a three-lever arm mechanism. Affixed to first distal portion 35 and first tubular section 20 are two anchoring devices 52 and 53. Anchoring device 52 is affixed to first distal portion 35, whereas anchoring device 53 is affixed to first tubular section 20. Anchoring devices 52 and 53 are preferably molded to hub assembly unit 10. However, other suitable attachment procedures known in the art may also be utilized. Anchoring devices 52 and 53 additionally provide an attachment point for first lever arm 54 and second lever arm 56, respectively. First lever arm 54 and second lever arm 56 are both comprised of a generally rigid material and have a proximal end and a distal end. The proximal ends of both lever arms 54 and 56 are pivotally attached to their corresponding anchoring device. The distal end of first lever arm 54 is hinged 58 to a portion of second lever arm 56. Second lever arm 56, therefore, is preferably longer than first lever arm 54. The third lever arm within lever style fine adjustment mechanism 50 includes the portion of hub assembly unit 10 wherein second distal portion 37 is slidably disposed within the lumen of first tubular section 20. Because the third lever arm is comprised of two slidably disposed portions, the third lever arm is variable in length.

A physician operates lever style fine adjustment mechanism 50 by raising and lowering distal end 57 of second lever arm 56. Raising distal end 57 of second lever arm 56 slidably displaces second distal portion 37 within first tubular section 20. As a result, the length of hub assembly unit 10 decreases. Lowering distal end 57 of second lever arm 56, on the other hand, slidably displaces second distal portion 37 apart from first tubular section 20. With this lever arm movement, the length of hub assembly unit 10 increases. Lever style fine adjustment mechanism 50, therefore, provides a physician with a medical device for finely adjusting the positioning of a second medical device 30. More specifically, lever style fine adjustment mechanism 50 allows a physician to precisely position a stent delivery catheter without the concern of a potential energy release associated with coarse adjustments.

Movement within the lever style fine adjustment mechanism 50 occurs in a single plane. All lever arms are hinged or fixed to operate within this single plane. As a result, little to no rotation occurs while extending and contracting the variable length third arm of hub assembly unit 10. Second distal portion 37 may be slidably disposed within the lumen of the first tubular section 20 in a oval shaped, a rectangular shaped or a triangular shaped lumen design to further prevent rotation within lever style fine adjustment mechanism 50, as described in detail with reference to FIGS. 3, 4 and 5.

Figure 7:
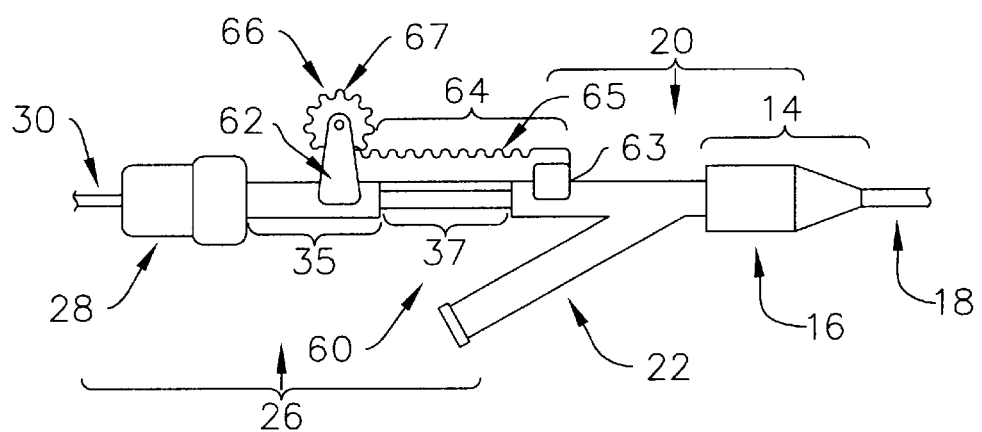
FIG. 7 shows a side elevation view of an alternative embodiment of the hub assembly unit of the present invention comprising a rack and pinion style fine adjustment mechanism.

Referring now to FIG. 7, wherein a side elevation view of an alternative embodiment of hub assembly unit 10 is shown comprising a rack and pinion style fine adjustment mechanism 60. Rack and pinion style fine adjustment mechanism 60 similarly comprises a portion of the proximal-most end of first tubular section 20 and a distal portion of second tubular section 26. The distal portion of second tubular section 26 additionally includes two distinct regions, a first distal portion 35 and a second distal portion 37, both having lumens running the length therein. First distal portion 35 attaches at a proximal end to hemostasis valve 28, or other fitting capable of maintaining the position and orientation of a second medical device 30 inserted the length therethrough. Second distal portion 37, on the other hand, is hemostatically, slidably disposed within the lumen of first tubular section 20. The two sections maintain a fluid connection between proximal end 12 to distal end 14 of hub assembly unit 10 because second distal portion 37 is hemostatically, slidably disposed within first tubular section 20.

With particularity to rack and pinion style fine adjustment mechanism 60, a rack 64 spans between first tubular section 20 and second tubular section 26. Rack 64 is characterized by a row of teeth 65 that extent outwardly away from the body of hub assembly unit 10. A first end of rack 64 is affixed to first tubular section 20 by first anchoring element 63. The second end of rack 64 is slidably affixed to first distal portion 35 by second anchoring element 62 and pinion 66. Second anchoring element 62 is affixed to first distal portion 35. Attached to second anchoring element 62 is pinion 66. Pinion 66 comprises a cogwheel having a series of teeth 67 on the rim of pinion 66. Through engagement with complementary teeth 65 of rack 64, pinion 66 transmits a horizontal motive force to rack 64. To aid in slidably disposing rack 64 through pinion 66 rotation, a recessed track incorporating a friction-reducing surface may be added to first distal portion 35.

A physician operates rack and pinion style fine adjustment mechanism 60 by rotating pinion 66 on rack 64. With respect to FIG. 7, rotation of pinion 66 in a clockwise fashion slidably displaces second distal portion 37 within first tubular section 20. As a result, the length of hub assembly unit 10 decreases. Rotation of pinion 66 in a counter-clockwise fashion, on the other hand, slidably displaces second distal portion 37 apart from first tubular section 20, thereby lengthening hub assembly unit 10. Rack and pinion style fine adjustment mechanism 60, therefore, provides a physician with a medical device for finely adjusting a second medical device 30 within a patient's vasculature. More specifically, rack and pinion style fine adjustment mechanism 60 allows a physician to precisely position a second medical device 30 without backlash, which is commonly associated with coarse manual adjustments.

Referring now to FIG. 8, wherein a cross-sectional elevation view of another embodiment of hub assembly unit 10 is shown having a slot and key style fine adjustment mechanism 70. Slot and key style fine adjustment mechanism 70 is comprised of a partial key element 71 (see FIG. 9), a slotted track element 80 (see FIG. 10) and a threading nut element 90 (see FIG. 11).

FIG. 9 illustrates, in detail, partial key element 71. Partial key element 71 comprises a first tubular section 72 having a proximal end, a distal end and a lumen 102 running the length therethrough. Affixed along a portion of first tubular section 72 is a partially threaded key 74. Partially threaded key 74 is preferably molded onto, or is a part of first tubular section 72. Partially threaded key 74 comprises raised threaded sections 76 and further comprises two first planar surfaces 78. First planar surfaces 78 are manufactured on partially threaded key 74 in a parallel relationship. The distance between first planar surfaces 78 further define a width for partially threaded key 74.

At the distal end of first tubular section 72 is a seal, such as an O-ring 34. O-ring 34 engages both the distal end of first tubular section 72 and the lumen wall of second tubular section 82 of slotted track element 80. When the distal end of first tubular section 72 is slidably displaced along the length of the lumen of second tubular section 82, O-ring 34 hemostatically prevents blood or other bodily fluids from being displaced between the outer wall of first tubular section 72 and the inner wall of second tubular section 82.

FIG. 10 illustrates a detailed perspective view of slotted track element 80. Slotted track element 80 comprises a second tubular section 82 having a proximal end 83, a distal end and a lumen extending the length therethrough. Proximal end 83 terminates into a first washer-like disc 84 that extends radially from second tubular section 82. At a location distal from proximal end 83 is a second washer-like disc 85 that additionally extends radially from second tubular section 82. Between first washer-like disc 84 and second washer-like disc 85 is slotted track 86.

Slotted track 86 comprises a portion of second tubular section 82 preferably having a first and a second opening. It is, however, recognized that a single opening could also be utilized. First and second openings possess identical widths and lengths and are additionally positioned on opposing sides of second tubular section 82. The widths of first and second openings are substantially the same as the distance between first planar surfaces 78 defining the width of partially threaded key 74. As such, partially threaded key 74 may be slidably disposed with slotted track 86 when positioned therein.

In order to position partially threaded key 74 within slotted track 86, slotted track element 80 includes a line of separation 88. Line of separation 88 extends along a portion of the length of slotted track element 80, dividing slotted track 86 into two sections. Once the two sections of slotted track element 80 are separated, first tubular section 72 is disposed within second tubular section 82. Partially threaded key 74 is then advanced to and aligned within the separated sections of slotted track 86. Once properly aligned within the separated section of slotted track 86, the two separated sections are again re-adhered.

Threading nut element 90 is positioned between first and second washer-like discs 84 and 85. Additionally, threading nut element is displaced over partially threaded key 74. In this configuration, threading nut element 90 provides a horizontal motive force upon partial key element 71 when rotated. FIG. 11 illustrates a detailed perspective view of threading nut element 90. In a preferred embodiment, the length of threading nut element 90 is equivalent to the length between first and second washer-like discs 84 and 85.

Threading nut element 90 includes two half sections 92 and 94. The inner lumen wall of half sections 92 and 94 include a machine threading 96. Machine threading 96 complementarily matches threading 76 on partially threaded key 74. Threading nut element 90 further comprises at least one press-fit pin 98 and its complementarily recessed hole 100. Press-fit pin 98 is positioned on half section 92 to properly align threading 96 between the two half sections 92 and 94. Proper alignment is important to provide a smooth continuous threading when the two half sections 92 and 94 are adhered. Press-fit pin 98 interference fits within recessed hole 100 in half section 94 to additionally prevent separation of half section 92 and 94 during operation.

Referring back to FIG. 8, luer connection 17 connects hub assembly unit 10 to a first medical device (not shown). In preferred embodiments, the first medical device is a catheter, and more specifically, a guide catheter. Additional attaching mechanisms between hub assembly unit 10 and the guide catheter, being known in the art, are also incorporated as within the scope of the present invention. In an alternative embodiment, hub assembly unit 10 is permanently affixed to the structure of the guide catheter.

Proximally from luer connector 17 is second tubular section 82 of hub assembly unit 10. Second tubular section 82 comprises a proximal end, a distal end and a lumen extending the length therethrough. As illustrated in FIG. 8, second tubular section 82 further includes channel 104 for partial key element 71 to be slidably displaced therein.

Although not shown, second tubular section 82 may comprise a means for securing hub assembly unit 10 during a medical procedure. Proper operation of hub assembly unit 10 requires maintaining hub assembly unit 10 in a single position, relative to the patient, during a medical procedure. A suture ring (not shown), may mechanically maintain the hub assembly unit's positioning during the medical procedure. Other mechanical means such as tape and clamps may likewise be used to secure hub assembly unit 10 during the medical procedure.

Extending from the proximal end 83 of second tubular section 82 is a portion of partial key element 71, specifically first tubular section 72. The proximal end of first tubular section 72 includes a hemostasis valve (not shown) or other fitting capable of maintaining the position and orientation of a second medical device inserted therein. The second medical device is advanced to a desired region within a patient's vasculature by initially inserting the second medical device into the proximal end of first tubular section 72. The second medical device is then advanced through the lumen of first tubular section 72, through the lumen of second tubular section 82, and finally through the lumen of the guide catheter until finally reaching a desired region within the patient's vasculature. In one embodiment of the present invention, the second medical device is a stent delivery catheter. In an alternative embodiment of the present invention, the second medical device is a balloon dilation catheter.

The distal end of partial key element 71 additionally extends into slot and key style fine adjustment mechanism 70. FIG. 8 illustrates the positioning of partially threaded key 74 within slotted track 86 of slot and key style fine adjustment mechanism 70. FIG. 8 further illustrates the positioning of threading nut element 90 between first and second washer-like discs 84 and 85, and further over partially threaded key 74.

A physician operates slot and key style fine adjustment mechanism 70 by rotating threading nut element 90, when assembled as shown in FIG. 8. When threading nut element 90 is rotated, complementary threads 96 guide partially threaded key 74 either up or down slotted track 86. Since partially threaded key 74 is merely a portion of first tubular section 72, movement of partially threaded key 74 translates as an extension or a contraction of hub assembly unit 10 as a whole. The length of hub assembly unit 10, therefore, may be extended or contracted by the proper rotation of threading nut element 90, thereby allowing a physician to precisely position a second medical device 30 at a desired point within a desired region of a patient's vasculature.

Extension and contraction of hub assembly unit 10 is proportional to the pathlength with which partially threaded key 74 may travel within slotted track 86. In preferred embodiments, slot and key style fine adjustment mechanism 70 may expand or contract the length of hub assembly unit 10 by a total of 0.5 to 3 centimeters. Most preferably, hub assembly unit 10 may be displaced a total of 1 to 2 centimeters. Each rotation of threaded nut element 90 correlates to an incremental displacement of hub assembly unit 10. The length of incremental displacement associated with each rotation is a product of the size of the threading on partially threaded key 74 and complementary threads 96 on threaded nut element 90. Finer threading provides for small incremental displacements for each rotation. In preferred embodiments, each rotation of threaded nut element 90 spatially displaces hub assembly unit by 1 to 6 millimeters.

Refer now to FIG. 12, wherein a transverse cross-sectional view of slot and key style fine adjustment mechanism 70 is shown. FIG. 12 further illustrates the spatial relationships between partial key element 71, slotted track element 80 and threading nut element 90. In particular, FIG. 12 illustrates partially threaded nut 74 within slotted track element 80.

Numerous characteristics and advantages of the invention covered by this document have been set forth in the foregoing description. It will be understood, however, that this disclosure is, in many respects, only illustrative. Changes may be made in details, particularly in matters of shape, size and ordering of steps without exceeding the scope of the invention. The invention's scope is of course defined in the language in which the appended claims are expressed.

What is claimed is:

1. A hub assembly, comprising:
   a first tubular element having a proximal end and a distal end with a lumen extending therethrough, the distal end of the first tubular element attaching to a first medical device;
   a second tubular element having a proximal end and a distal end with a lumen extending therethrough, the proximal end of the second tubular element receiving and engaging a second medical device; and
   a fine adjustment mechanism comprising a turnbuckle mechanism, wherein the fine adjustment mechanism extends or contracts the hub assembly from a first length to a second length.

2. The hub assembly of claim 1, wherein the first tubular element comprises a Y-adapter.

3. The hub assembly of claim 1, wherein the second tubular element is hemostatically, slidably disposed within the lumen of the first tubular element.

4. The hub assembly of claim 1, wherein the first tubular element is hemostatically, slidably disposed within the lumen of the second tubular element.

5. The hub assembly of claim 1, wherein the second tubular element includes a hemostasis valve, the hemostasis valve maintains the position and orientation of the second medical device.

6. The hub assembly of claim 1, wherein the fine adjustment mechanism may expand or contract the hub assembly from the first length to the second length by a total of 1 to 2 centimeters.

7. The hub assembly of claim 1, wherein the fine adjustment mechanism may expand or contract the hub assembly from the first length to the second length in 1 to 6 millimeter increments.

8. The hub assembly of claim 1, wherein a suture ring is attached to the hub assembly.

9. The hub assembly of claim 1, wherein the first medical device comprises a guide catheter.

10. The hub assembly of claim 1, wherein the second medical device comprises a stent delivery catheter.

11. The hub assembly of claim 1, wherein the second medical device comprises a balloon dilatation catheter.

12. A hub assembly, comprising:
    a first tubular element having a proximal end and a distal end with a lumen extending therethrough, the distal end of the first tubular element attaching to a first medical device;
    a second tubular element having a proximal end and a distal end with a lumen extending therethrough, the proximal end of the second tubular element receiving and engaging a second medical device; and
    a fine adjustment mechanism that extends or contracts the hub assembly from a first length to a second length, wherein at least a portion of the lumen of the first tubular element is non-circular.

13. A hub assembly, comprising:
    a first tubular element having a proximal end and a distal end with a lumen extending therethrough, the distal end of the first tubular element attaching to a first medical device;
    a second tubular element having a proximal end and a distal end with a lumen extending therethrough, the proximal end of the second tubular element receiving and engaging a second medical device; and
    a fine adjustment mechanism that extends or contracts the hub assembly from a first length to a second length, wherein at least a portion of the lumen of the second tubular element is non-circular.

14. A hub assembly, comprising:
    a first tubular element having a proximal end and a distal end with a lumen extending therethrough, the distal end of the first tubular element attaching to a first medical device;

a second tubular element having a proximal end and a distal end with a lumen extending therethrough, the proximal end of the second tubular element receiving and engaging a second medical device; and a fine adjustment mechanism comprising a rack and pinion mechanism wherein the fine adjustment mechanism extends or contracts the hub assembly from a first length to a second length.

15. A catheter assembly for placing and positioning a medical device within a body, the catheter assembly comprising:

a catheter shaft having a proximal end, a distal end and a lumen extending the length therethrough;

a hub assembly having a lumen therethrough in fluid communication with the catheter shaft lumen, the hub assembly having a proximal end and a distal end, the distal end of the hub assembly affixed to the proximal end of the catheter shaft and the proximal end of the hub assembly permitting passage of additional medical devices therethrough and permitting engagement of the additional medical devices therewith; and a fine adjustment mechanism comprising a turnbuckle mechanism capable of extending or contracting the hub assembly from a first length to a second length.

16. The catheter of claim 15, wherein the hub assembly includes a hemostasis valve, the hemostasis valve adapted to maintain the position and orientation of the additional medical devices.

17. The catheter of claim 15, wherein the fine adjustment mechanism may expand or contract the hub assembly from the first length to the second length by a total of 1 to 2 centimeters.

18. The catheter of claim 15, wherein the fine adjustment mechanism may expand or contract the hub assembly from the first length to the second length in 1 to 6 millimeter increments.

19. The catheter of claim 15, wherein the additional medical device comprises a balloon dilation catheter.

20. The catheter of claim 15, wherein the additional medical device comprises a stent delivery catheter.

21. A catheter assembly for placing and positioning a medical device within a body, the catheter assembly comprising:

a catheter shaft having a proximal end, a distal end and a lumen extending the length therethrough;

a hub assembly having a lumen therethrough in fluid communication with the catheter shaft lumen, the hub assembly having a proximal end and a distal end, the distal end of the hub assembly affixed to the proximal end of the catheter shaft and the proximal end of the hub assembly permitting passage of additional medical devices therethrough and permitting engagement of the additional medical devices therewith; and a fine adjustment mechanism comprising a rack and pinion mechanism.

* * * * *